United States Patent
Scott et al.

(10) Patent No.: US 11,786,362 B2
(45) Date of Patent: Oct. 17, 2023

(54) STABLE IOL BASE DESIGN TO SUPPORT SECOND OPTIC

(71) Applicant: Alcon Inc., Fribourg (CH)

(72) Inventors: James M. Scott, Weatherford, TX (US); Raza Shah, Arlington, TX (US)

(73) Assignee: Alcon Inc., Fribourg (CH)

( * ) Notice: Subject to any disclaimer, the term of this patent is extended or adjusted under 35 U.S.C. 154(b) by 274 days.

(21) Appl. No.: 17/231,438

(22) Filed: Apr. 15, 2021

(65) Prior Publication Data

US 2021/0322150 A1 Oct. 21, 2021

Related U.S. Application Data

(60) Provisional application No. 63/010,745, filed on Apr. 16, 2020.

(51) Int. Cl.
 A61F 2/16 (2006.01)

(52) U.S. Cl.
 CPC ............ *A61F 2/1648* (2013.01); *A61F 2/164* (2015.04); *A61F 2/1618* (2013.01); *A61F 2/1645* (2015.04); *A61F 2002/1681* (2013.01)

(58) Field of Classification Search
 CPC .................................................... A61F 2/1648
 See application file for complete search history.

(56) References Cited

U.S. PATENT DOCUMENTS

| 4,562,600 | A | 1/1986 | Ginsberg et al. |
| 7,569,073 | B2 | 8/2009 | Vaudant et al. |
| 8,858,626 | B2 | 10/2014 | Noy |
| 9,364,316 | B1 | 6/2016 | Kahook |
| 2003/0114927 | A1* | 6/2003 | Nagamoto ............ A61F 2/1613 623/6.37 |
| 2004/0059414 | A1 | 3/2004 | Green |
| 2010/0204787 | A1* | 8/2010 | Noy ...................... A61F 2/1648 623/6.34 |
| 2010/0204788 | A1* | 8/2010 | Van Noy ............... A61F 2/1694 623/6.37 |
| 2011/0130833 | A1 | 6/2011 | Scott et al. |
| 2011/0295367 | A1 | 12/2011 | Cuevas |

(Continued)

FOREIGN PATENT DOCUMENTS

| AU | 2015380300 A1 | 8/2017 |
| WO | 2005032427 A1 | 4/2005 |

OTHER PUBLICATIONS

Hara et al., "Preventing Posterior Capsular Opacification with an Endocapsular Equator Ring in a Young Human Eye", Arch. Ophthalmol., Apr. 2007, 125(4): 483-486.

(Continued)

*Primary Examiner* — Javier G Blanco
(74) *Attorney, Agent, or Firm* — Patterson + Sheridan, LLP (57) ABSTRACT

An intraocular lens (IOL) configured to support a first optic for functioning as a single lens IOL and configured to support a second optic for functioning as a dual optic IOL. The base includes a first optic for providing a base power. A recess in an anterior rim of the base is configured for positioning a radial extension of a second optic. The geometry of the recess is configured to securely couple to the radial extension to prevent rotation of the second optic relative to the base and prevent tilting of the second optic relative to an optic axis.

11 Claims, 4 Drawing Sheets

(56) References Cited

U.S. PATENT DOCUMENTS

| | | | |
|---|---|---|---|
| 2012/0330415 A1* | 12/2012 | Callahan | A61F 2/1694 623/6.43 |
| 2016/0030161 A1* | 2/2016 | Brady | A61F 2/1648 623/6.13 |
| 2017/0042667 A1* | 2/2017 | Collins | A61F 2/1694 |
| 2017/0319332 A1* | 11/2017 | Kahook | A61F 2/16 |
| 2018/0147049 A1* | 5/2018 | Park | A61F 2/1613 |
| 2018/0271645 A1* | 9/2018 | Brady | B29D 11/026 |
| 2018/0368971 A1 | 12/2018 | Zacher | |
| 2019/0374334 A1 | 12/2019 | Brady et al. | |

OTHER PUBLICATIONS

Kavoussi et al., "Prevention of capsular bag opacification with a new hydrophilic acrylic disk-shaped intraocular lens", JCRS 2011; 37: 2194-2200.

Leishman et al., "Prevention of capsular bag opacification with a modified hydrophilic acrylic disk-shaped intraocular lens", JCRS 2012; 38: 1664-1670.

Werner L. et al., "Interlenticular opacification: Dual-optic versus piggyback intraocular lenses", Journal Cataract Refractive Surgery, Apr. 2006, 32:655-661.

* cited by examiner

STABLE IOL BASE DESIGN TO SUPPORT SECOND OPTIC

PRIORITY CLAIM

This application claims the benefit of priority of U.S. Provisional Patent Application Ser. No. 63/010,745 titled "STABLE IOL BASE DESIGN TO SUPPORT SECOND OPTIC," filed on Apr. 16, 2020, whose inventors are James M. Scott and Raza Shah, which is hereby incorporated by reference in its entirety as though fully and completely set forth herein.

FIELD

The present disclosure relates generally to the field of intraocular lenses (IOLs) and more particularly to a base with a first optic and capable of supporting a second optic as part of a multi-part optical system.

BACKGROUND

The human eye functions to provide vision by transmitting light through a clear outer portion called the cornea and focusing the image by way of a crystalline lens onto a retina. The quality of the focused image depends on many factors including the size and shape of the eye, and the transparency of the cornea and the lens.

When age or disease causes the lens to become less transparent (e.g., cloudy), vision deteriorates because of the diminished light, which can be transmitted to the retina. This deficiency in the lens of the eye is medically known as a cataract. An accepted treatment for this condition is surgical removal of the lens from the capsular bag and placement of an artificial intraocular lens (IOL) in the capsular bag. In the United States, the majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The diseased lens, once removed, is replaced by an IOL.

Some conventional IOLs are single focal length IOLs, while others are multifocal IOLs. Single focal length IOLs have a single focal length or single power. Objects at the focal length from the eye/IOL are in focus, while objects nearer or further away may be out of focus. Although objects are in perfect focus only at the focal length, objects within the depth of field (within a particular distance of the focal length) are still acceptably in focus for the patient to consider the objects in focus. Multifocal IOLs, on the other hand, have at least two focal lengths. For example, a bifocal IOL has two focal lengths for improving focus in two ranges: a far focus corresponding to a larger focal length and a near focus corresponding to a smaller focal length. Thus, a patient's distance vision and near vision may be improved.

SUMMARY

Embodiments of a multi-part intraocular lens (IOL) disclosed herein are unique in that the base can support a first optic to provide vision correction but can also support a second optic to provide additional vision correction.

The base comprises a continuous posterior rim with a discontinuous anterior rim. The discontinuity defines at least one recess for supporting a radial extension of a second optic.

A multi-part IOL has a unique geometry to interlock the second optic to the base. Embodiments benefit a patient by allowing the second optic to be added at a future date and allowing the second optic to be removed independently of the first optic. The second optic can be an electro-optic lens capable of autofocusing for near accommodation, a toric IOL, or an additional single or multi-focal lens for higher power needs (e.g., greater than 30 D).

Embodiments overcome the challenges of creating a stable optical unit composed of a base and two optics that can be assembled and disassembled in the capsular bag by a surgeon. A multi-part IOL minimizes the cross-sectional area to allow for a smaller incision than incisions necessary for full IOLs. A multi-part IOL with an interlocking geometry allows easy assembly and disassembly in the capsular bag while preventing misalignment, decentration, rotation or tilting.

A multi-part IOL with a larger anterior-posterior height applies a circumferential force to the capsular bag.

Furthermore, a multi-part IOL with a separation distance between two optics may result in low intralenticular opacification (ILO). Low ILO performance may be due in part to any one or a combination of mechanisms, including but not limited to the height of an IOL, the shape of the base, mechanical forces being applied by the anterior and posterior rims, separation of the first and second optics, and increased flow of aqueous humor through the base and IOL.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of ±10% in a stated value, numeric or otherwise, unless other variations are indicated.

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown but is to be accorded the widest scope consistent with the principles and features described herein.

I. Multi-Part IOL—Overview

Figure 1:
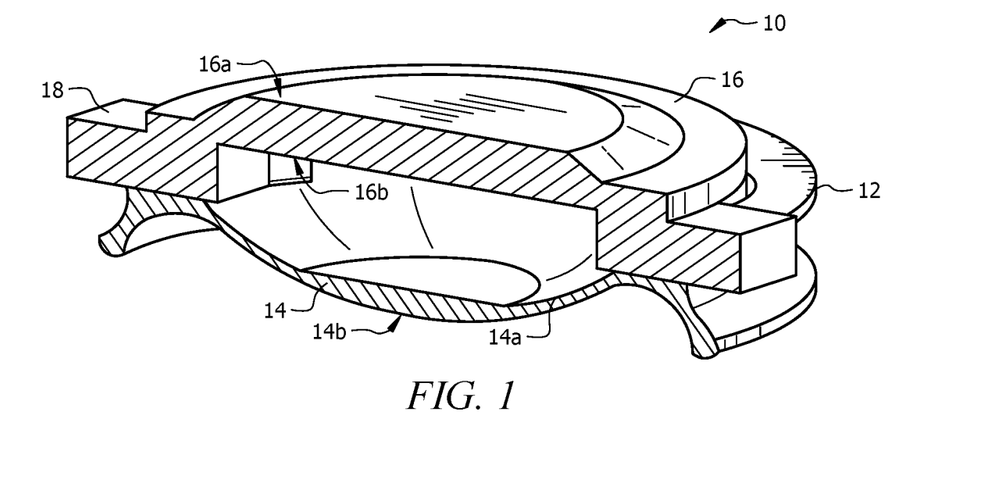
FIG. 1 depicts a perspective cutaway view of an IOL including a base design to support two optics.

FIG. 1 depicts a perspective cutaway view of a multi-part intraocular lens (IOL) 10 comprising a base 12 with first optic 14 arranged posterior to second optic 16. As depicted in FIG. 1, first optic 14 is formed integral with base 12 and second optic 16 comprises one or more radial extensions 18 for coupling to base 12, discussed below in more detail.

As depicted in FIG. 1, first optic 14 is formed with a thickness defined by anterior surface 14*a* with a radius of curvature and posterior surface 14*b* with a radius of curvature. First optic 14 may be selected to provide a base power, astigmatism correction and/or other vision correction(s). First optic 14 may be aspheric and/or toroidal and have the same or different curvatures on anterior surface 14*a* and posterior surface 14*b*. First optic 14 may be monofocal, extended-depth-of-focus, or multifocal, and may include other characteristics that are not shown or discussed in detail for simplicity (e.g., blue-light filtering).

In a multi-part IOL 10, second optic 16 may be removably coupled to base 12, so as to piggy-back over, in front of, or on top of the first optic 14. Second optic 16 may provide additional base power, provide near vision accommodation, or may provide correction for other eye condition(s). One or more radial extensions 18 may prevent rotation or tilt of second optic 16 relative to base 12.

Also visible in FIG. 1, IOL 10 is configured such that posterior surface 16*b* of second optic 16 is separated from anterior surface 14*a* of first optic 14, discussed below in more detail.

II. Base with First Optic for Use in Single Lens IOL or in Multi-Part IOL

Figure 2:
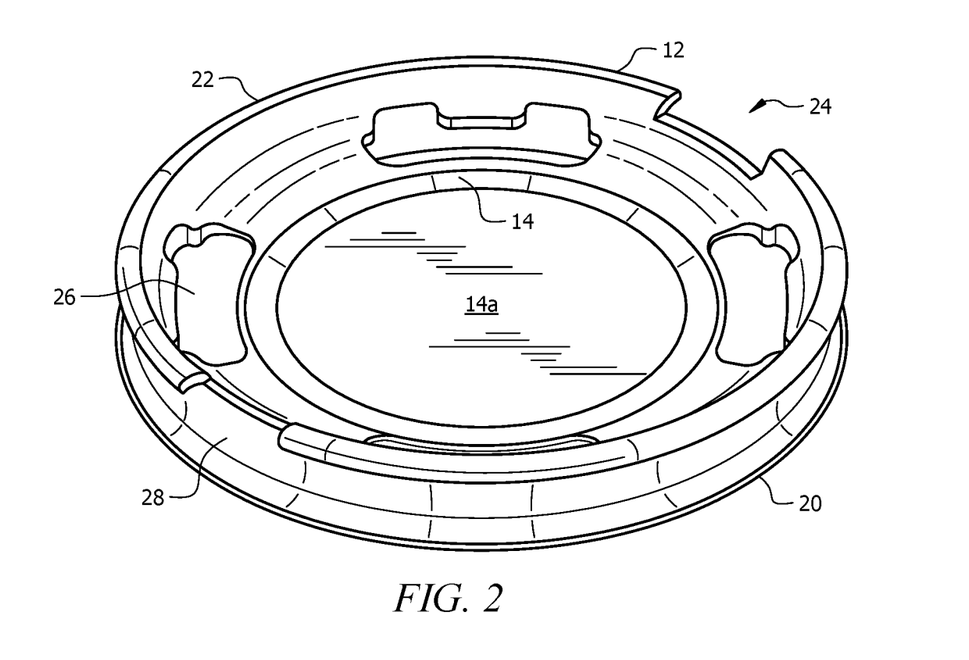
FIG. 2 depicts a perspective view of a first optic supported by a base having a continuous posterior rim and a discontinuous anterior rim formed with a pair of recesses.

FIG. 2 depicts a perspective view of base 12 having first optic 14 for implanting in a capsular bag as a single lens IOL 10. Base 12 comprises continuous posterior rim 20 configured for coupling with first optic 14 and discontinuous anterior rim 22.

Posterior rim 20 may be shaped to prevent migration of lens epithelial cells (LECs) and/or bias first optic 14 in an anterior or posterior region of a capsular bag. The base 12 may also form a continuous ring on the surface of a posterior capsule of the eye and apply a circumferential force to the capsular bag when inserted, while maintaining an open capsular bag configuration to reduce or prevent posterior capsular opacification (PCO). The geometry of the base 12 may also be adapted to elevate and/or separate the anterior capsule from portions of the IOL 10. For example, the shape and/or a height of the anterior rim 22 around the circumference of the base 12 may be effective in supporting the anterior capsule or reducing the degree that the anterior capsule may be compressed on or around portions of the IOL 10. Thus, in some embodiments, both the posterior rim 20 and the anterior rim 22 may be sized and configured to separate the capsular bag from portions of the IOL 10 once the IOL 10 is inserted into the eye. One or more haptics (not shown) may be coupled to anterior rim 22 or posterior rim 20 of base 12.

Anterior rim 22 and posterior rim 20 may be arranged about, and connected by, a circumferential surface 28 with a cross-section profile that may be straight or curved. In some embodiments, one or both of the anterior rim 22 and the posterior rim 20 may comprise a portion that extends along the anterior-posterior direction, which may form the circumferential surface 28. As depicted in FIG. 2, anterior rim 22 and posterior rim 20 form a concave circumferential surface 28. In other embodiments, anterior rim 22 and posterior rim 20 may form a convex circumferential surface 28. Base 12 formed from a resilient material and having a concave or convex circumferential surface 28 may allow base 12 to conform to a capsular bag for improved patient comfort and apply mechanical forces to the capsular bag, discussed below.

First optic 14 may be made of a variety of optical materials including but not limited to one or more of silicone, a hydrogel, an acrylic, Alcon AcrySof®, and Alcon Clareon®. First optic 14 may be formed as a symmetric disc defined by a single radius of curvature. In some embodiments, first optic 14 is formed asymmetrically with a first radius of curvature along a first axis and a second radius of curvature along a second axis. In other embodiments, first optic 14 is configured for specific eye conditions. A radius of curvature for anterior surface 14*a* or posterior surface 14*b* may be defined over the diameter of first optic 14 or for a diameter less than the diameter of first optic 14. Base 12 may be configured with openings 26 between first optic 14 and posterior rim 20 to allow aqueous humor to flow through base 12.

In some embodiments, base 12 coupled with first optic 14 may be inserted via a small incision in the capsular bag such that IOL 10 has a single optic 14 and functions as a single lens IOL assembly. The design of base 12 and the ability to separately insert the base 12 from a second optic 16 may also allow for minimization of the incision size required for implantation. Base 12 may include features (not shown) to provide access for a probe (e.g., Sinskey hook) intra-operatively, which allows the base 12 to be more easily manipulated.

Still referring to FIG. 2, base 12 comprises an anterior rim 22 adapted to support second optic 16. In particular, anterior rim 22 comprises one or discontinuities defining one or more recesses 24. One or more recesses 24 formed in anterior rim 22 may be sized and shaped to interlock with radial extensions 18 of second optic 16, as herein. In some examples, one or more recesses 24 comprise a notch, depression, or cutout in anterior rim 22. Anterior rim 22 may be the anterior-most feature of base 12, and one or more recesses 24 may define a surface posterior to the anterior rim 22 such that the anterior-most surface of base 12 (e.g., anterior surface of anterior rim 22) is discontinuous. Moreover, one or more recesses 24 may be located in anterior rim 22 such that an outermost circumference of the anterior-most structure (e.g., outermost circumference of anterior rim 22) of base 12 is discontinuous. Hence, discontinuities in anterior rim 22 may be deviations from otherwise continuous surfaces or features in radial and/or anterior-to-posterior directions. In these and other examples, discontinuities defined by one or more recesses 24 may have the same radius of curvature as the anterior rim 22.

III. Multi-Part IOL with Two Optics

Figure 3:
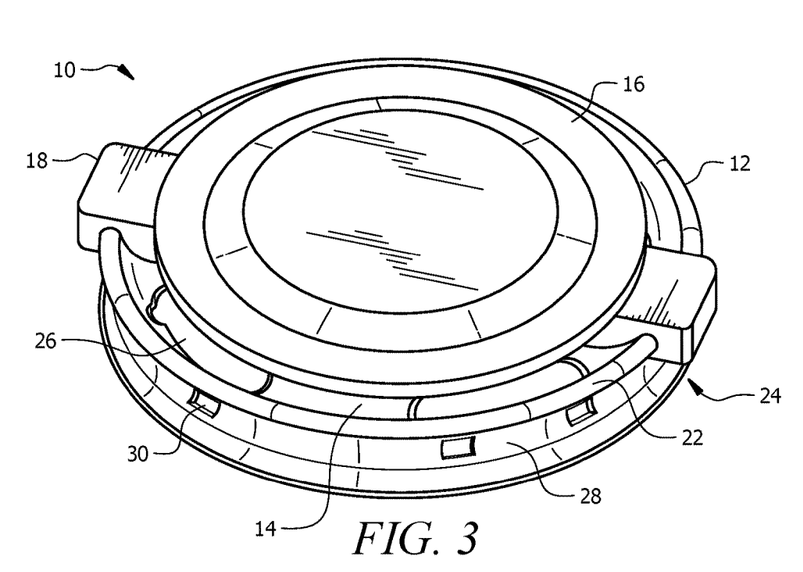
FIG. 3 depicts a perspective view of an IOL with a base supporting a first optic and a second optic with radial extensions positioned in recesses on the anterior rim of the base.

FIG. 3 depicts a perspective view of IOL 10 with second optic 16 removably coupled to base 12. IOL 10 may include second optic 16 for customizing IOL 10 to address a specific patient condition or multiple conditions. As shown in FIG. 3, second optic 16 may have an outer diameter less than an inner diameter of anterior rim 22, such that anterior rim 22 surrounds optic 16. In some examples, second optic 16 comprises a diameter sufficiently smaller in size than the inner diameter of anterior rim 22 so as to allow aqueous humor to flow through IOL 10 when inserted and assembled in an eye. The second optic 16 of IOL 10 further includes one or more radial extensions 18, which may be sized and shaped to extend through, rest on, and/or seat within recesses 24 of anterior rim 22 of the base 12 such that, when the IOL 10 is assembled, the radial extensions 18 of the second optic 16 rest anterior to and/or are positioned against an anterior-facing surface of the one or more recesses 24. Base 12 with openings 26 between first optic 14 and posterior rim 20 and openings 30 in one or more of anterior rim 22 and posterior rim 20, such as in the circumferential surface 28, also allow aqueous humor to flow through IOL 10. The ability for aqueous humor to flow through IOL 10 may decrease the rate of intralenticular opacification (ILO) in IOL 10.

Figure 4:
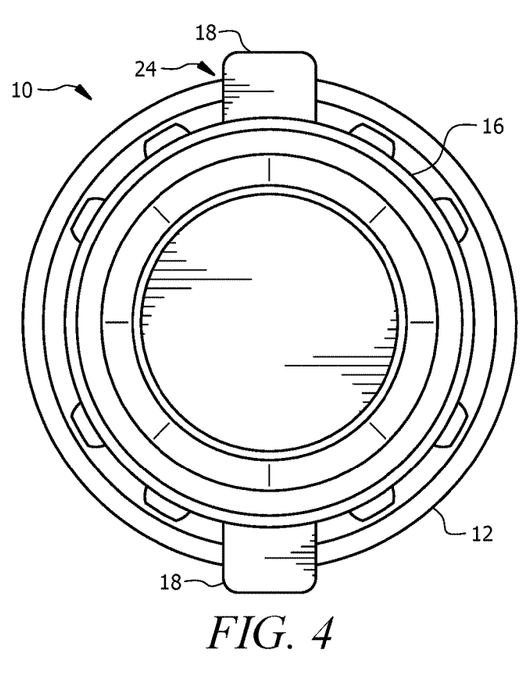
FIG. 4 depicts a top view of an IOL with straight radial extensions extending outward of the base.
Figure 5:
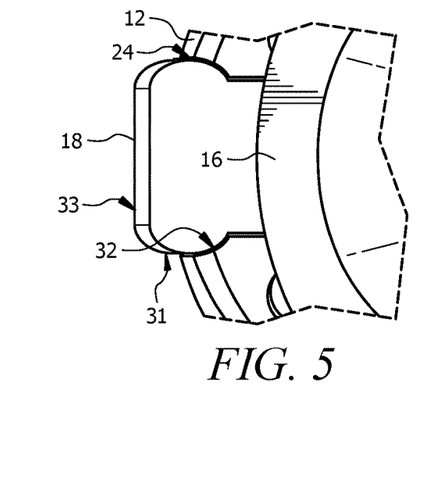
FIG. 5 depicts a top close-up view of a portion of an IOL with radial extensions formed in a dog bone shape and extending outward of the base.

IV. Multi-Part IOL is Configured for Supporting Different Radial Extension Geometries FIG. 4 depicts a top view and FIG. 5 depicts a partial top view of embodiments of IOL 10 with second optic 16 having radial extensions 18 with different geometries. In some embodiments, each of the one or more radial extensions 18 of an optic 16 (and one or more recesses 24 in base 12 corresponding to radial extensions 18) may have the same geometry and/or dimensions. In other embodiments, radial extensions 18 of optic 16 (and one or more recesses 24 in base 12 corresponding to radial extensions 18) may have different geometries and/or dimensions such that second optic 16 can be positioned in base 12 in only one orientation. In the examples shown, each of the one or more radial extensions 18 are configured to contact sides of one or more recesses 24, or interlock with the recesses 24, to prevent rotation, tilting, and/or decentration of second optic 16 relative to base 12. One or more of the radial extensions 18 may extend radially beyond an outer circumference of base 12 (which may be defined, for example, by an outer circumference of anterior rim 22 or posterior rim 20) when IOL 10 is assembled. Certain embodiments of second optic 16 include two radial extensions 18 that are diametrically opposite. Certain embodiments of second optic 16 may include only one radial extension 18. In some embodiments, radial extensions 18 may include haptics (not shown) for stabilizing or positioning second optic 16 or IOL 10. In some embodiments, one or more radial extensions 18 may include electronic components capable of providing accommodation or otherwise assist with improving patient vision.

Referring to FIG. 4, one or more recesses 24 in base 12 may be configured with parallel sides and a substantially flat anterior-facing surface. Complementary geometry of one or more radial extensions 18 may also be configured with parallel sides and a substantially flat posterior surface to facilitate secure positioning within recesses 24.

Referring to FIG. 5, one or more recesses 24 in base 12 may be configured with non-parallel (e.g., angled or curved) sides 32 such that a distance between each side 32 of a given recess 24 varies radially. In the example of FIG. 5, second optic 16 comprises radial extension 18 having a dog-bone geometry in which each side 31 of extension 18 is characterized by a convex curve connected by a radially outermost surface 33 (which may be curved or straight). In the exemplary embodiment of FIG. 5, recess 24 accordingly includes concavely curved sizes 32 sized and shaped to receive and interlock with the convex sides of radial extension 18. In other examples, radial extension 18 and recess 24 may have other complementary geometries or shapes for securing and stabilizing second optic 16 in base 12. In some embodiments, radial extension 18 may be configured such that radially outermost surface 33 is substantially flush with the outer perimeter of anterior rim 22 of base 12 in the radial and/or anterior-to-posterior directions when assembled. In such embodiments, the one or more radial extensions 18 may not extend outward of or beyond the perimeter of base 12 in an assembled configuration. Furthermore, radial extension 18 having a dog bone shape may be positioned in other recesses 24 having other geometries.

V. Multi-Part IOL with Base Structure for Supporting Various Optics

Figure 6:
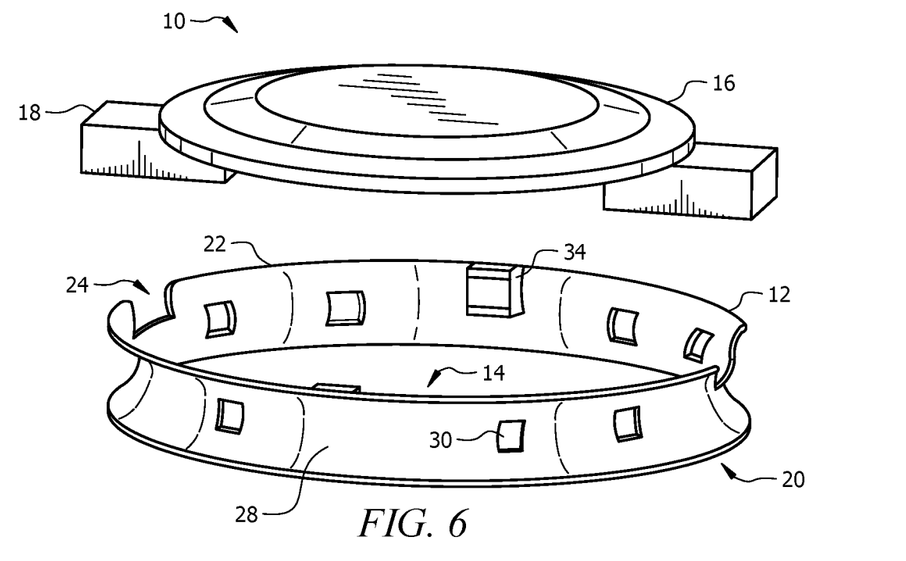
FIG. 6 depicts a perspective exploded view of an IOL with a base formed with pedestals for supporting a second optic.

Base 12 is configured to support various types of second optics 16. FIG. 6 depicts a perspective exploded view of one embodiment of IOL 10 comprising base 12 with first optic 14 and second optic 16 positioned for coupling to base 12. Anterior rim 22 includes one or more recesses 24 for receiving one or more radial extensions 18 of second optic 16. As depicted in FIG. 6, embodiments of base 12 may also include one or more pedestals 34. Pedestals 34 may provide additional stability and support for second optic 16. Anterior rim 22 may be formed with an anterior surface for seating second optic 16. One or more of the anterior surface of anterior rim 22, recesses 24 and pedestals 34 are configured for supporting second optic 16, including preventing rotation, decentration, tilting and/or misalignment of second optic 16 within base 12 and relative to first topic 14.

Base 12 is configured to support various types of second optics 16. Second optic 16 depicted in FIG. 6 may comprise an electro-optic lens capable of full (distance-to-near) vision correction and one or more radial extensions 18 comprise an hermetically sealed electronic housing containing electroactive components (e.g., one or more processors, sensors, and/or a battery or other power source) adapted to control second optic 16. For example, the second optic 16 may be an electro-optic lens capable of autofocusing to provide continuous near-to-distance vision accommodation. In other examples, second optic 16 may comprise a monofocal, aspheric, toric, multifocal, extended-depth-of-focus, and/or other accommodating lens. Using multiple optics, IOL 10 allows customization of IOL 10 to meet a patient's specific eye condition. In some instances, the modular arrangement of IOL 10 allows for improved customization of vision. For example, a base 12 may be implanted in a first surgery to provide base power correction for distance vision. Subsequently (e.g., after sufficient time for healing and fixation of the lens position in the eye), a second optic 16 may be selected and implanted to correct or enhance the patient's vision. For example, a second optic 16 may be implanted to add or decrease power for corrected distance vision in the case of refractive miss. In other examples, second optic 16 may be added to correct astigmatism, spherical or chromatic aberrations, provide multi-focality or extended depth of focus for intermediate and/or near vision, and/or to provide accommodation for improved range of vision. In each instance, the optical performance and characteristics of second optic 16 are complementary to those of the first optic 14, and actual performance of first optic 14 in a particular patient may considered in selecting second optic 16. Alternatively, IOL 10 may be initially implanted with two optics, and second optic 16 may be removed and, if desired, replaced with a different second optic 16 in a subsequent procedure. Recesses 24 may also be configured to receive haptics (not shown).

Still referring to FIG. 6, base 12 includes anterior rim 22 coupled to posterior rim 20 with an outer circumferential surface 28, wherein a cross-section profile of the anterior rim 22, the posterior rim 20 and the circumferential surface 28 depicted in FIG. 6 is a concave structure. Base 12 may include openings 30 in anterior rim 22 or posterior rim 20, which allow aqueous humor to flow through base 12 when inserted in an eye. The cross-section profile of base 12 and openings 30 that allow aqueous humor to flow through IOL 10 may be based on a particular type of second optic 16.

Figure 7:
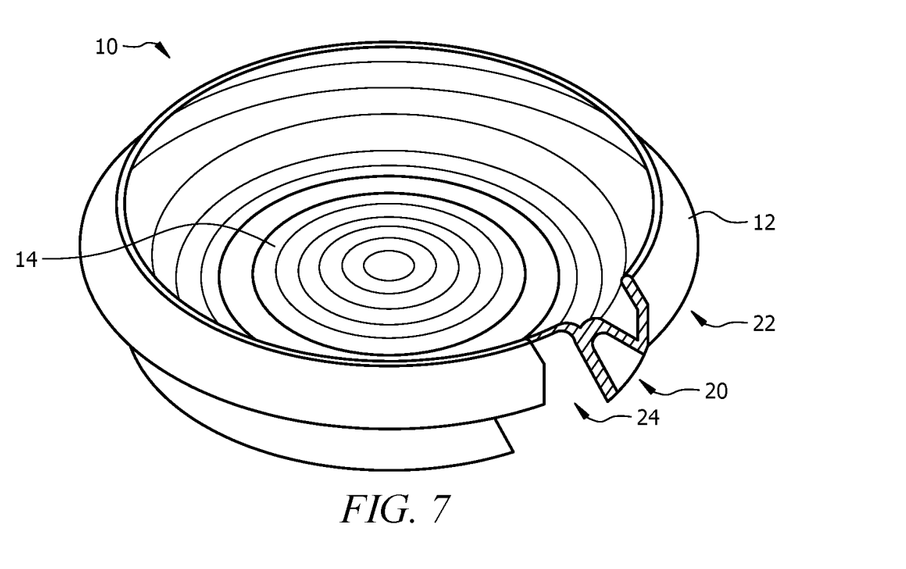
FIG. 7 depicts a perspective view of a base with a discontinuity in the posterior rim and the anterior rim, the discontinuities comprising a recess in the posterior rim and a recess in the anterior rim.

Referring now to FIG. 7, an alternative base 12 may be formed to support first optic 14 and to support an additional optic, such as second optic 16 (not shown). An alternative design may be necessary based on the condition of the eye or the structure of second optic 16. For example, a patient may benefit from base 12 having a more continuous surface and second optic 16 may benefit from additional electronic components that increase the thickness of one or more radial extensions 18. FIG. 7 depicts a perspective view of IOL 10 in which base 12 is formed with discontinuous posterior rim 20 and discontinuous anterior rim 22, with a discontinuity on posterior rim 20 and a discontinuity on anterior rim 22 forming recess 24. Base 12 depicted in FIG. 7 may be formed with first optic 14 integral with posterior rim 20. Anterior rim 22 may have a first cross-section profile and posterior rim 20 may have a second profile. Each of anterior rim 22 and posterior rim 20 may have a concave, convex, linear or angled cross-section profile.

VI. Multi-Part IOL has Greater Height without Patient Discomfort

Figure 8:
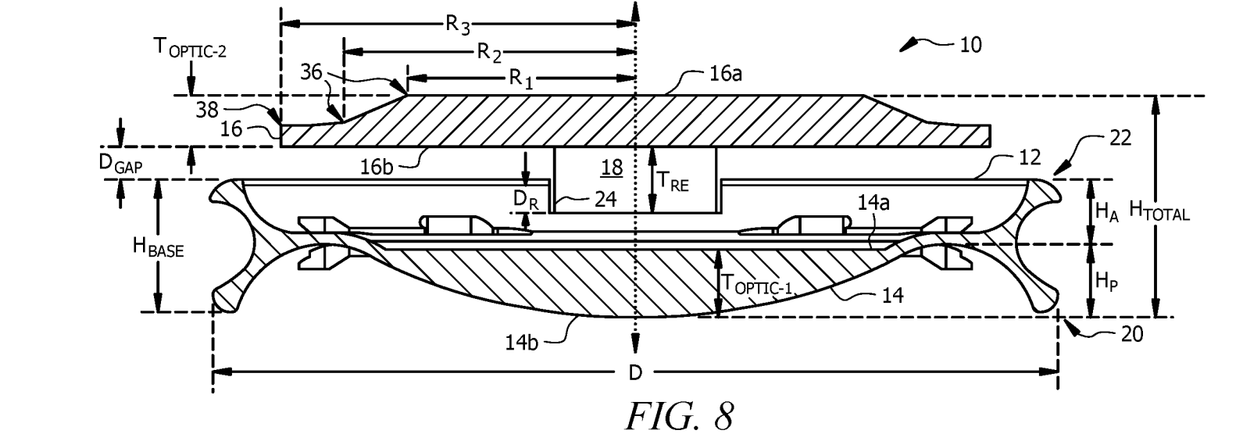
FIG. 8 depicts a cutaway side view of an IOL with an adjustable second optic seated on the radial extensions.
Figure 9:
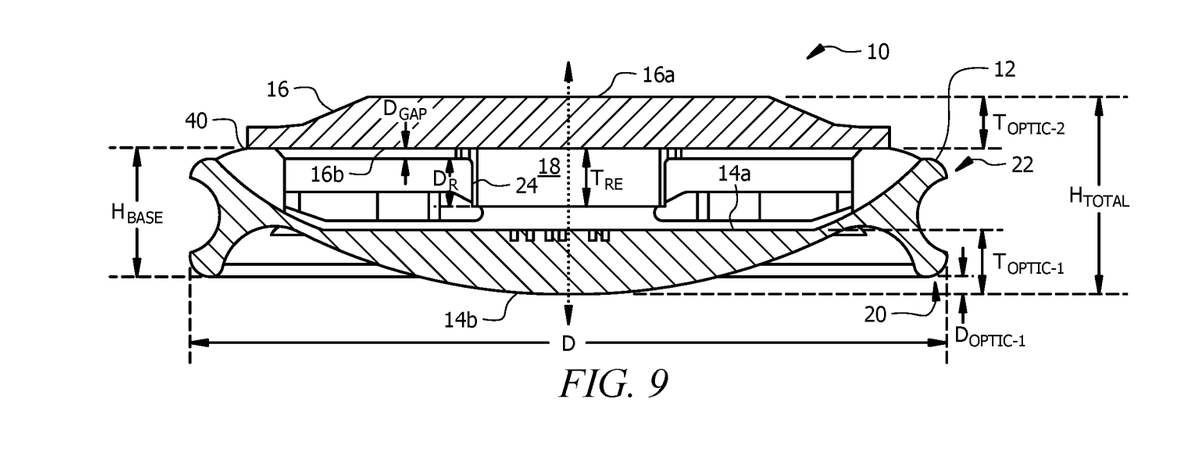
FIG. 9 depicts a cutaway side view of an IOL with an adjustable second optic seated on structures integral with the base.

Referring to FIGS. 8 and 9, IOL 10 may be formed with a larger height without affecting patient comfort. As depicted in FIG. 8, second optic 16 is seated on radial extensions 18 such that second optic 16 is separated from anterior rim 22 by a gap ($D_{Gap}$). A total height ($H_{Total}$) of IOL 10 in FIG. 8 may be calculated based on the thickness of second optic 16 ($T_{Optic-2}$) plus any separation between second optic 16 and base 12 ($D_{Gap}$) plus a height of base 12 ($H_{Base}$). Referring to FIG. 8, second optic anterior surface 16a may be configured to lower opacification rates of IOL 10. Second optic anterior surface 16a may be configured to include one or more angled transitions 36 at radial distances ($R_1$) and ($R_2$) and an angled edge 38 at radial distance ($R_3$).

As seen in FIG. 9, in another embodiment, posterior surface 16b of second optic 16 may be seated on pedestals 40 integral with base 12 such that there is still some clearance ($D_{GAP}$) between posterior surface 16b of second optic 16 and anterior rim 22. Also depicted in FIG. 9, posterior surface 14b of first optic 14 may have a large radius of curvature such that first optic 14 extends a greater distance beyond a posterior surface of posterior rim 20. In another embodiment (not shown), second optic 16 may be seated on an anterior surface of anterior rim 22 such that no gap exists between second optic 16 and anterior rim 22. Accordingly, a total height ($H_{Total}$) of IOL 10 in FIG. 9 may be calculated based on the thickness of second optic 16 ($T_{Optic-2}$) plus a height of base 12 ($H_{Base}$) plus the thickness of first optic 14 that extends beyond posterior rim 20 ($D_{Optic-1}$).

As can be seen from FIGS. 8 and 9, the total height of IOL 10 may depend on the height of base 12 ($H_{Base}$) (which may depend on the height of anterior rim 22 ($H_A$) plus the height of posterior rim 20 ($H_P$)). The total height of IOL 10 may also depend on the thickness of one or more of first optic 14 and second optic 16, which may depend on the radius of curvature of posterior surface 14b of first optic 14 and anterior surface 16a of second optic 16, respectively. The total height of IOL 10 may also depend on any gap between base 12 and second optic 16 ($D_{GAP}$), which may depend on the depth of recesses 24 ($D_R$) and the thickness of radial extensions 18 ($T_{RE}$). In some embodiments, the total height ($H_{Total}$) of IOL 10 may be a height in a range greater than 1.0 millimeter and less than 3.2 millimeters.

In some embodiments, IOL 10 may be configured with a height to diameter ratio to maintain separation between the anterior and posterior capsular bag, while avoiding causing irritation to the eye. The height may vary depending on the modulus of the materials. For example, selected height dimensions specified in this disclosure may be based on the modulus of hydrophobic and hydrophilic acrylic IOLs. Softer IOL materials, like low modulus silicone, may have higher heights and still will not cause irritation in the eye. In some embodiments of IOL 10, it may be particularly important that the height of the IOL 10 be within a particular range at outer radial distances, or around the circumference, of the IOL 10. More specifically, the height of the base 12 ($H_{Base}$) at outer radial distances along the IOL 10 should be within a dimensional range, such that the height of the base 12 ($H_{Base}$) is both great enough to provide rigidity and support for maintaining separation of the anterior and posterior capsules, while also remaining below a particular height threshold. Heights that exceed a particular threshold may result in undesirable forces to the anterior and posterior capsules, which may result in irritation of the capsular bag and eye, or other unwanted side effects.

For example, in some embodiments, it may be important that for radial distances greater than approximately 3.5 millimeters from a center-point or optical axis of the IOL 10 towards the outer periphery or circumference of the base 12, that the height of the IOL 10, which for some radial distances may be the total height of the IOL 10 ($H_{Total}$) as defined above, not exceed approximately 1.3 millimeters. In some embodiments, it may be preferable that the height of the IOL 10 for radial distances greater than approximately 3.5 millimeters be in a range of 0.7 millimeters to 1.2 millimeters. However, in some embodiments, IOL 10 may have a height, which for some radial distances may be total height ($H_{Total}$), greater than 1.3 millimeters for radial distances that are less than 3.5 millimeters from a center-point, or optic axis, of the IOL 10.

In some embodiments, as depicted in FIGS. 8 and 9, the diameter (D) of the base 12 may be in a range of 7.6 millimeters to 8.6 millimeters, or possibly between 8.0 millimeters and 8.2 millimeters, which may be greater than a diameter of the second optic 16, with the exception of one or more radial extensions 18 of the second optic 16. Thus, in some embodiments, the height of the IOL 10 at some radial distances greater than 3.5 millimeters from the center-point or optic axis of the IOL 10 may comprise only the height of the base 12 ($H_{Base}$), or possibly the height of the base 12 ($H_{Base}$) plus a portion of the thickness of a radial extension 18 ($T_{RE}$). Therefore, the height of the base 12 ($H_{Base}$), or the height of the base 12 ($H_{Base}$) plus a portion of the thickness of a radial extension 18 ($T_{RE}$), should not exceed 1.3 millimeters, or more specifically may be in a range of 0.7 millimeters to 1.2 millimeters. The exemplary dimensions, such as the height and diameter ranges, discussed above may also apply to other embodiments, in addition to those discussed with respect to FIGS. 8 and 9.

VII. Separation of Optics to Inhibit ILO

Also seen in FIGS. 8 and 9, embodiments of IOL assembly 10 are configured to maintain a separation between first optic 14 and second optic 16, which may reduce or inhibit intralenticular opacification (ILO).

Referring to FIG. 8, second optic 16 may be supported by radial extensions 18 seated in recesses 24 such that anterior surface 14a of first optic 14 is separated from posterior surface 16b of second optic 16 based on a depth of recesses 24 ($D_R$) and a thickness of radial extensions 18 ($T_{RE}$).

Referring to FIG. 9, posterior rim 20 may be coupled to first optic 14 and base 12 may have a height ($H_{Base}$) such that anterior surface 14a of first optic 14 is separated from posterior surface 16b of second optic 16 based on a position of first optic 14 in posterior rim 20 and a height of anterior rim 22. Maintaining a separation between first optic 14 and second optic 16 allows aqueous humor to flow through IOL 10, which may decrease the rate of intralenticular opacification (ILO) in IOL 10. The separation distance between two optics may depend on materials used to manufacture the optics. For example, for hydrophobic acrylic IOL material such as the AcrySof® material, the separation (gap) may be important. Embodiments of IOL 10 formed with a hydrophobic acrylic IOL material may be configured to separate second optic 16 from first optic 14 by a distance in a range of 0.25 millimeters to 0.75 millimeters. More specifically, in some embodiments, the posterior surface 16b of the second optic 16 may be separated from the anterior surface 14a of the first optic 14 by a distance in a range of 0.25 millimeters to 0.75 millimeters. The distance between the two optics may be less important if the two optics are of different materials. For example, if one optic is silicone and one is AcrySof® material, first optic 14 may touch second optic 16.

A separation distance between first optic 14 and second optic 16 may depend on either or both of a radius of curvature of anterior surface 14a of first optic 14 or a radius of curvature of posterior surface 16b of second optic 16. A small radius of curvature for either anterior surface 14a of first optic 14 or posterior surface 16b of second optic 16 will tend to reduce the separation distance, whereas a larger radius of curvature for either anterior surface 14a of first optic 14 or posterior surface 16b of second optic 16 will tend to increase the separation distance.

VIII. Delivery/Implantation of Multi-Part IOL

A multi-part IOL 10, including base 12 with first optic 14 and second optic 16, may be implanted using various surgical techniques. A multi-part IOL 10 may be implanted by initially delivering base 12 into the capsular bag in a rolled or folded configuration using an injector (a.k.a., inserter or delivery tube) inserted through a corneal incision, through the capsulorhexis, and into the capsular bag.

Base 12 may be ejected from the injector and allowed to unfurl. With gentle manipulation, haptics (not shown) of base 12 may engage the inside equator of the lens capsule and may center base 12 relative to the capsulorhexis. Openings 26 of the posterior rim 20 and rim openings 30 may facilitate handling of base 12.

In some embodiments, first optic 14 is integral with base 12 such that implanting base 12 positions first optic 14. In other embodiments, first optic 14 is formed separate from base 12. In these embodiments, first optic 14 may also be delivered in a rolled or folded configuration using an injector, positioning the distal tip thereof adjacent base 12. First optic 14 may be ejected from the injector and allowed to unfurl. With gentle manipulation, first optic 14 may be centered relative to the capsulorhexis. First optic 14 may have features (not shown) for ease of insertion into a capsular bag, for removal of first optic 14 from a capsular bag, and to help align first optic 14 relative to base 12. Once first optic 14 has been delivered and unfurled in the capsular bag, first optic 14 may be connected to base 12 by seating first optic 14 in posterior rim 20 of base 12.

Once first optic 14 is connected to base 12, second optic 16 may also be delivered in a rolled or folded configuration using an injector, positioning the distal tip thereof adjacent base 12. Second optic 16 may be ejected from the injector and allowed to unfurl. With gentle manipulation, second optic 16 may be centered relative to the capsulorhexis. Second optic 16 may have features (not shown) for ease of insertion into a capsular bag and to help align second optic 16 relative to base 12. Once second optic 16 has been delivered and unfurled in the capsular bag, second optic 16 may be connected to base 12, which may include one or more of seating posterior surface 16b of second optic 16 on anterior rim 22 or pedestals 34 on the inside surface of anterior rim 22 and positioning radial extensions 18 in recesses 24 on anterior rim 22.

If needed, IOL 10 including base 12, first optic 14 and second optic 16, may be removed by generally reversing the steps described above. A probe or similar device may enter the capsular bag containing multi-part IOL 10. With gentle manipulation, second optic 16 may be lifted such that second optic 16 and base 12 are disconnected. The probe may remove one or more of second optic 16 and base 12. If first optic 14 and base 12 are formed as separate pieces, first optic 14 may be lifted such that first optic 14 and base 12 are disconnected. The probe may remove one or more of first optic 14 and base 12.

A multi-part intraocular lens (IOL) with a base for supporting a first optic and further capable of supporting a second optic at a distance from the first optic has been described. The apparatuses, systems, and methods have been described in accordance with the exemplary embodiments shown, and one of ordinary skill in the art will readily recognize that there could be variations to the embodiments, and any variations would be within the spirit and scope of the apparatuses, systems, and methods. Accordingly, many modifications may be made by one of ordinary skill in the art without departing from the spirit and scope of the appended claims.

We claim:

1. A multi-part intraocular lens (IOL) comprising:
a ring-shaped base component comprising:
   a first optic comprising an anterior surface and a posterior surface;
   a continuous posterior rim supporting the first optic therebetween;
   an anterior rim comprising an anterior surface defining at least two recesses; and
   a concave circumferential outer surface extending from the anterior rim to the continous posterior rim; and
a second optic comprising an anterior surface, a posterior surface, and at least two diametrically opposed radial extensions extending peripherally from an optical zone of the second optic, the at least two diametrically opposed radial extensions adapted to fit within the at least two recesses to couple the second optic to the ring-shaped base,
wherein each of the at least two recesses comprise a geometry complementary to a geometry of each of the at least two diametrically opposed radial extensions,
wherein the continuous posterior rim is sized and shaped to prevent migration of lens epithelial cells (LECs) when the IOL is implanted.

2. The multi-part IOL of claim 1, wherein the at least two diametrically opposed radial extensions are adapted to interlock with the at least two recesses such that each radial extension fits between sidewalls of a corresponding recess of the at least two recesses and rests on top of an anterior surface of the corresponding recess.

3. The multi-part IOL of claim 2, wherein each of the at least two diametrically opposed radial extensions comprises a dog-bone geometry.

4. The multi-part IOL of claim 1, wherein the first optic provides a base power correction.

5. The multi-part IOL of claim 4, wherein the second optic provides a near vision correction.

6. The multi-part IOL of claim 5, wherein the second optic comprises one of a fixed focal length optic, an aspheric optic, a toric optic or an electro-optic.

7. The multi-part IOL of claim 1, wherein at least one radial extension comprises an electronic component.

8. The multi-part IOL of claim 1, wherein at least one radial extension comprises a haptic.

9. The multi-part IOL of claim 1,
wherein the anterior surface of the anterior rim and a posterior surface of the continuous posterior rim define a base height of at least 0.7 millimeters at a radial distance of at least 3.5 millimeters.

10. The multi-part IOL of claim 9, wherein the base height is at least 1.1 millimeters at a radial distance of at least 4.1 millimeters.

11. The multi-part IOL of claim 9, wherein the base height is at least 1.2 millimeters at a radial distance of at least 4.0 millimeters.

* * * * *